United States Patent [19]

Sauerbaum

[11] Patent Number: 5,391,986

[45] Date of Patent: Feb. 21, 1995

[54] APPARATUS FOR DETERMINING THE PROPORTION OF A SUBSTANCE HAVING PARAMAGNETIC PROPERTIES IN A MIXTURE OF SUBSTANCES

[75] Inventor: Thomas Sauerbaum, Gross Grönau, Germany

[73] Assignee: Drägerwerk Aktiengesellschaft, Lübeck, Germany

[21] Appl. No.: 56,771

[22] Filed: May 4, 1993

[30] Foreign Application Priority Data

May 9, 1992 [DE] Germany .................. 4215215

[51] Int. Cl.6 .................. G01N 27/74; G01R 33/12
[52] U.S. Cl. .................. 324/204; 23/25.02
[58] Field of Search .................. 324/204, 228, 262; 73/25.02

[56] References Cited

U.S. PATENT DOCUMENTS 3,537,713 11/1970 Prival .................. 324/204
4,950,984 8/1990 Otten et al. .

Primary Examiner—Walter E. Snow
Attorney, Agent, or Firm—Walter Ottesen

[57] ABSTRACT

The invention is directed to an apparatus for determining the component of paramagnetic substances such as oxygen. This determination is made with a magnetic field source and an even number arrangement of magnetic field cores, with each field core being surrounded by a measuring field coil for detecting the magnetic changing field generated by a rotatable cuvette. The apparatus is improved in that the formation of the magnetic stray fields is reduced and the component of the magnetic flux which is effective for measurement and which passes through the cuvette is increased. For this purpose, the cuvette is mounted in the housing of the apparatus in such a manner that its rotational plane partitions the housing into two component regions. The magnetic field source is arranged in one component region and the magnetic field cores and the measuring field coils corresponding thereto are arranged in the other component region of the housing.

7 Claims, 2 Drawing Sheets

APPARATUS FOR DETERMINING THE PROPORTION OF A SUBSTANCE HAVING PARAMAGNETIC PROPERTIES IN A MIXTURE OF SUBSTANCES

FIELD OF THE INVENTION

The invention relates to a paramagnetic gas detecting apparatus for determining the proportions of substances, especially of oxygen, having paramagnetic characteristics in a mixture of substances. The apparatus has a housing wherein the mixture is passed by an arrangement of an even number multiple of magnetic field sources by means of a cuvette rotatable by a drive shaft. The magnetic field of the magnetic field sources penetrates the cuvette. Each of the magnetic field sources includes a coil arrangement for converting the magnetic flux change into an electrical measuring signal. The magnetic flux change is caused in the cuvette by the paramagnetic substance. The magnetization polarity of the magnetic field sources and their respective measuring field coils is combined in alternate alignment with the magnetization polarity of the next adjacent magnetic field sources and their respective measuring field coils.

An apparatus of the kind described above is disclosed in U.S. Pat. No. 4,950,984 incorporated herein by reference.

BACKGROUND OF THE INVENTION

In the apparatus described above, a disc-shaped cuvette rotates within the apparatus housing along the end faces of four iron cores. The iron cores are each surrounded by measuring field coils and are seated on a permanent magnet. The permanent magnet generates the required magnetic field which penetrates the cuvette. The disc-shaped cuvette itself is provided with cutouts to which, for example, oxygen is supplied. The cuvette with the cutouts is guided past the magnetized iron cores by the rotational movement. As soon as the cuvette moves the oxygen past the iron cores, the magnetic flux in the cores increases because of the paramagnetism of the oxygen. This increase is detected by the coils surrounding the cores since the flux change induces a voltage in the coils which can be further processed as a measurement signal by an evaluation device connected to the coils.

The rotation of the cuvette causes an alternating magnetic flux to occur in the cores and therefore an alternating voltage across the coil. The path of the magnetic flux starts from the permanent magnet on which the iron cores are mounted and passes through the cores and the cuvette and continues through the housing walls and finally ends again at the permanent magnet. The strong magnetic fields are necessary for a sensitive measurement signal. For this reason, a polarization of the cores occurs on the one hand, and a polarization of the surrounding wall of the apparatus on the other hand, because of the one-sided arrangement and connection between the permanent magnet and the iron cores. In this way, large mutually close surfaces of opposing magnetic polarity are produced between the housing walls and the magnetic components so that a large portion of the magnetic flux is lost because of stray fields and does not flow through the rotating cuvette. This stray component can amount to up to 50%.

SUMMARY OF THE INVENTION

It is an object of the invention to improve a measuring apparatus of the kind described above so that the formation of magnetic stray fields is reduced and the component of the magnetic flux, which is effective for measurement and which passes through the cuvette, is increased.

According to a feature of the invention, the cuvette is accommodated in the apparatus housing so that its plane of rotation partitions the housing into two component regions. The magnetic field source is mounted in one of the component regions and areally covers approximately the entire cuvette in its extent along its plane of rotation. An even-number arrangement of cores is provided in the other component region, with the cores collecting the magnetic flux through the cuvette. Each of the cores is surrounded by a measuring field coil and these cores, in turn, are aligned in a direction toward the cuvette.

The advantage of the invention is seen essentially in that the path of the flux lines is concentrated through the cuvette because of the magnetic decoupling of the magnetic field sources and the cores surrounded by the respective measuring field coils. Also, the stray fields between the apparatus housing on the one hand, and the cores on the other hand, are reduced. Viewed magnetically, the housing parts and the cores have the same polarity so that the development of a stray field is suppressed between the housing parts and the cores.

A signal increase of up to 30% is achieved alone by the arrangement according to the invention of the magnetic field sources on the one hand, and the measuring field coils and cores corresponding thereto on the other hand. Because of the absence of the stray field, it is now also possible to extend the cores and the measuring field coils corresponding thereto as far as necessary in order to increase the signal sensitivity. This was not possible in the known apparatus described above, since an extension of the measuring field coils and the cores would also lead to an increase of the unwanted disturbing influence of the stray fields. Because of the good suppression of the stray field, it is now sufficient to provide only two measuring field coils and the cores corresponding thereto, which is in contrast to the known measuring apparatus. It is, however, here also purposeful to provide four or a higher even number of measuring field coils, and the cores corresponding thereto, for reasons of symmetry and for optimal utilization of the space which is available.

A further advantage of the invention is that it is no longer necessary to consider the magnetic characteristics of the remaining assembly components in connection with the rotatable cuvette. Accordingly, the bearing for the rotatable cuvette can now be mounted without further protective measures notwithstanding its self-magnetization qualities. This can be done without the measuring field coils being disturbed by the rotating magnetic field.

A ferromagnetic material having a high permeability is provided in a suitable manner as a magnetic field source. This material is subjected to a magnetic field by means of an electric coil, whereby the magnetic field lines of the magnetic field source penetrate into the ferromagnetic cores disposed on the opposite side of the cuvette. The magnetic field source then corresponds to the cuvette with respect to its extent so that the field lines act simultaneously via all electrical coils or cores.

When, during rotation of the cuvette, an alternating signal is generated with reference to the magnetic flux at one of the cores, a corresponding change of the field lines can be detected because of the uniform distribution of the field lines over all other cores. If in contrast, a permanent magnet is selected as the magnetic field source, then a plate of good magnetically-conducting material is placed as an equipotential disc on the surface of the permanent magnet facing toward the cuvette. A high permeable iron-cobalt alloy is appropriate as a suitable material for this purpose.

An especially advantageous cuvette arrangement includes a circular disc having cutouts symmetrical with respect to the rotational axis through which the substance mixture, such as the oxygen gas, can flow. These cutouts are so configured that for a position of one of the cutouts in which the end face of one of the cores is fully exposed, the next end face of the corresponding core remains excluded from the contour of the cutout. The sum of the cross sections of the end faces remain essentially constant with the end faces being only partially exposed in the course of the rotational movement by the contours of the cutouts.

The above configuration of the cuvette defines a diaphragm disc for controlling the magnetic flux. This configuration makes it possible that an approximately constant through-flow of the cuvette is achieved at each time point of the rotational movement. When one of the end faces of the cores appears completely in the cutout, then the next adjacent end face is still completely covered. As soon as the end face of the observed core is partially covered with the advancing rotation of the cuvette, a corresponding portion of the end face of the next adjacent core is partially exposed by the advancing cutout. In this way, the magnetic plate, in combination with the equipotential plate, acts as a source of constant magnetic voltage, which is the precondition for a measuring signal which has a magnitude as large as possible and which is free of fluctuation.

An especially advantageous form of the cutout contour is provided by circular annular segments, which extend concentrically to the rotational axis and which are so dimensioned that they completely expose the end faces of the cores, at least for a time during the rotation of the cuvette when the cuvette passes over these end faces.

A cutout contour which is equally effective is provided by a kidney-shaped cutout extending concentrically to the rotational axis.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
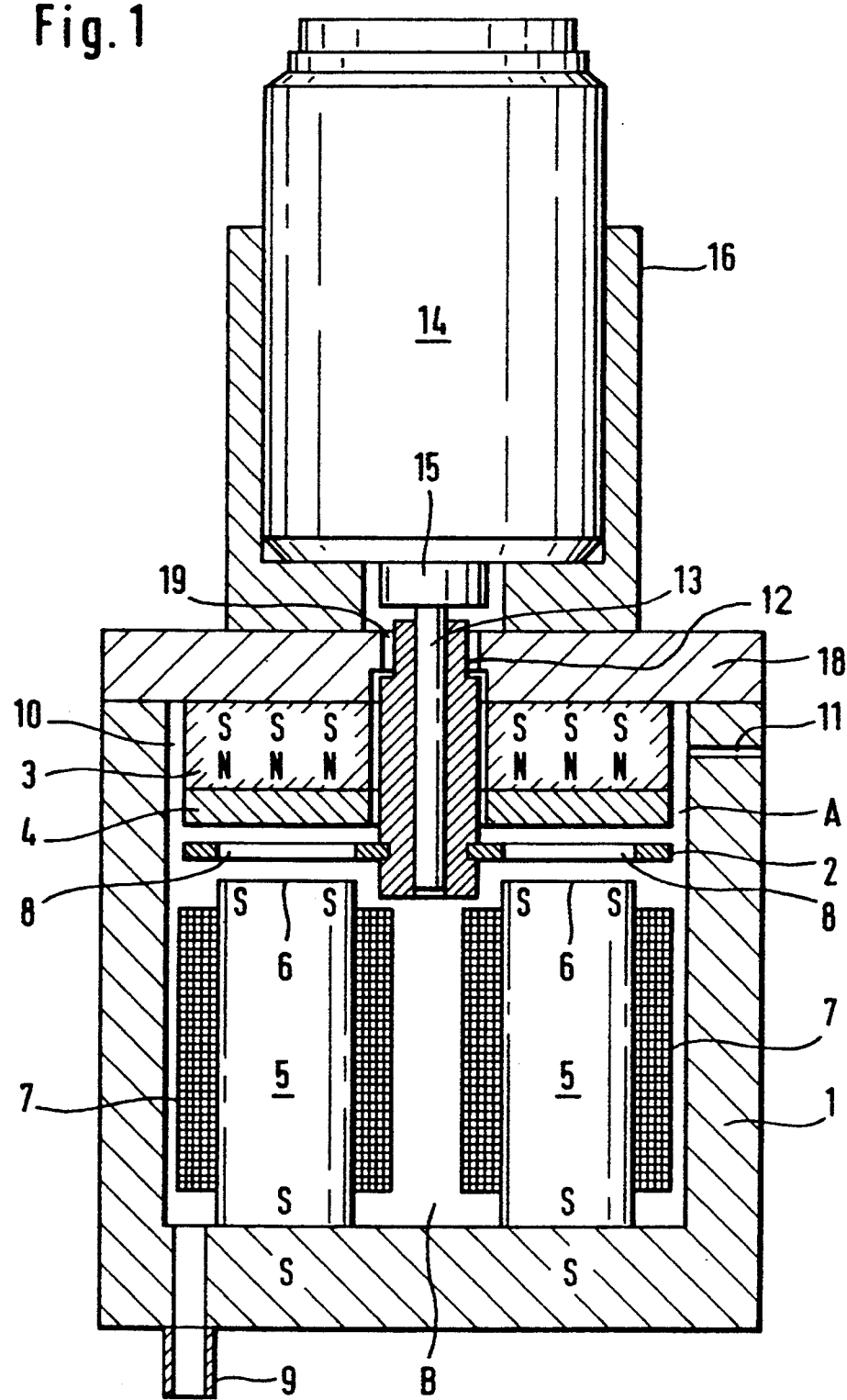
FIG. 1 is a side elevation view, in section, of a paramagnetic measuring apparatus according to an embodiment of the invention; and, FIG. 2 is a plan view of the cuvette of the measuring apparatus of FIG. 1 with the drive unit removed.

The measuring apparatus shown in FIG. 1 includes a housing 1 and a cuvette 2 in the form of a disc rotatably mounted on a shaft 13. The disc 2 is made of a material which is as magnetically inert as possible. The cuvette 2 partitions the interior space of the housing 1 into two component regions (A, B). The component region A includes a permanent magnetic plate 3 which is covered by an equipotential plate 4. Magnetic plate 3 and equipotential plate 4 extend in the same direction in housing 1 and have the same extent as the cuvette 2. Four cores 5 are provided in component region B of the housing 1 and only two of these cores are shown. The cores 5 are connected to the inner wall of the housing 1 in such a manner that their end faces 6 are directed toward the cuvette 2 and are as close as possible thereto. Each of the cores 5 is surrounded by a measuring field coil 7 and signal leads of the respective field coils are connected to an evaluation device (not shown).

Figure 2:
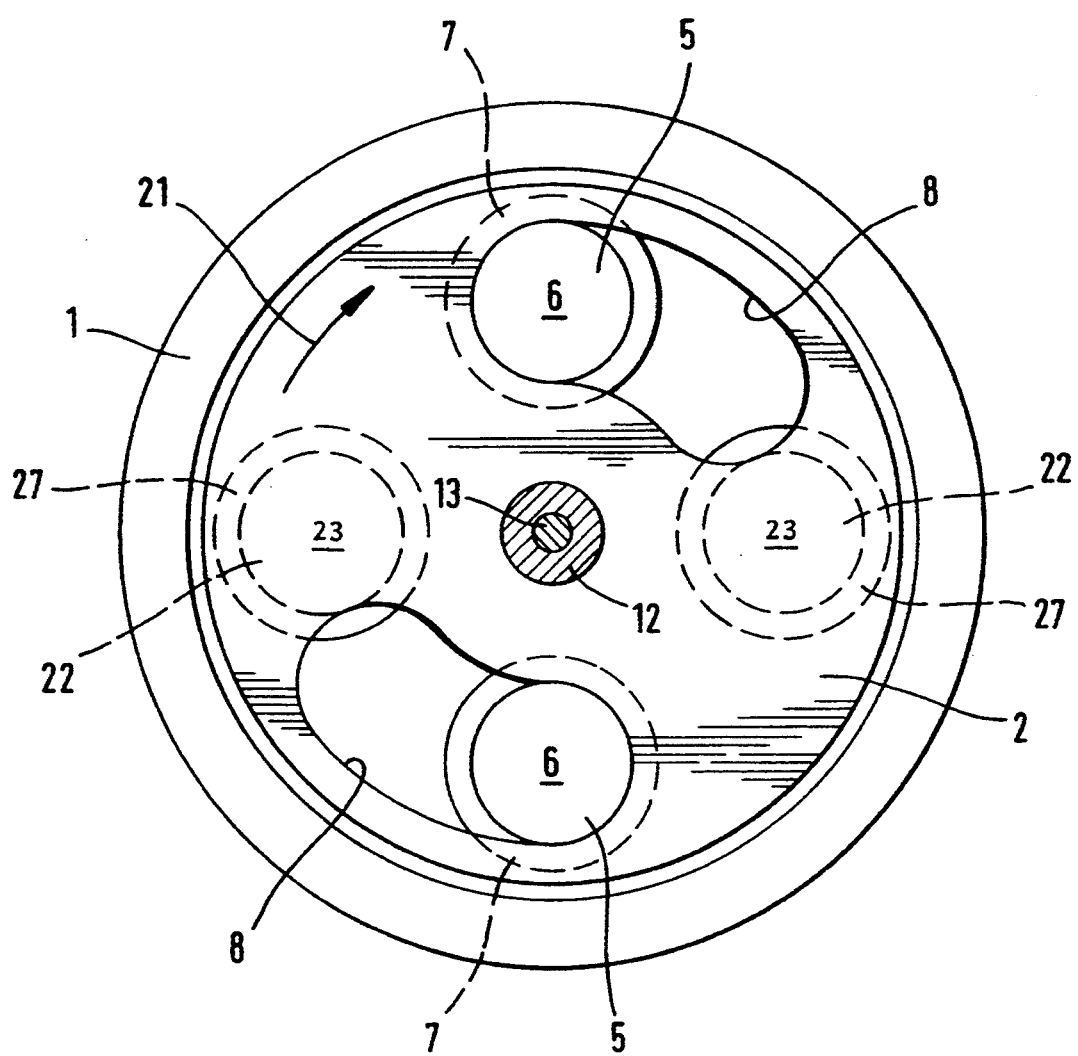

The cuvette 2 has cutouts 8 symmetrical with respect to the rotational axis and these cutouts expose the end faces 6 of two of the cores 5 in the position of the cuvette shown (see also FIG. 2). The cutouts 8 define respective cells and the interior space thereof is filled with the substance to the measured, the substance having paramagnetic characteristics. The substance to be measured can, for example, be oxygen. The substance to be measured is conducted into the interior of the housing 1 via a gas feed 9. This substance then fills out the interior of the housing and penetrates into the surrounding of the cutouts 8 which can be viewed as the measuring chamber 10. The substance then escapes to the ambient via an outlet passage 11.

The cuvette 2 is attached to a shaft collar 12 which, in turn, is attached to the shaft 13 of a drive motor 14 and is guided via a shaft bearing 15. The motor 14 and the motor mount 16 surrounding the motor 14 are connected to the housing wall 18. The wall 18 supports the magnetic plate 3 and has a break-through 19 for the shaft 13 and the shaft collar 12. The magnetic polarity of the magnetic plate 3 is represented by the capital letters N (North) and S (South). From the special arrangement of the magnetic plate 3, wall 18 and housing 1, it can be seen that the magnetic polarity S over the housing 1 remains the same in the cores 5 up to the end faces 6. In this way, the field coils 7 and the cores 5 are surrounded by a housing 1 of the site magnetic polarity S which the cores 5 exhibit.

FIG. 2 shows a plan view of the cuvette 2 with the drive unit comprising the motor 14 and motor mount 16 removed. The housing wall 18 together with the magnetic plate 3 attached thereto and the equipotential plate 4 are likewise removed. The cuvette 2 is mounted in the housing 1 so as to be rotatable by the shaft 13 in the direction of arrow 21. The cuvette 2 is configured as a disc and has two approximately kidney-shaped cutouts 8 lying radially opposite each other and which, in the position shown, completely expose the end faces 6 of the two cores 5. The next-adjacent cores 22 having respective measuring field coils 27 are just about to become visible within the contours of the respective cutouts 8 but are not yet exposed. With the rotation of the cuvette 2 in the direction of arrow 21, the core end faces 6 are reduced with respect to the clear pass-through through the cutouts 8 with the end faces 23 of the next-adjacent cores 22 becoming increasingly exposed in corresponding amounts in the cutouts 8 and, in this way, compensating for the flux of the magnetic fields which reduces because of the advancing covering of the core end faces 6. Thus, this compensation is achieved by the increasingly exposed magnetic fields of the cores 22.

The alternating winding sense of the measuring field coils (7, 27) causes the flux reductions produced in the coils 7 to generate a positive voltage because of the ever lesser penetration of the magnetic fields in the paramagnetic substance. Because of the alternating winding sense in the coils 27, the flux increase generated there by the increase of the flux pass-through through the cutouts 8 likewise leads to a positive voltage. In this way, a total measuring signal which remains essentially constant is obtained from the measuring signals of the four individual coils (7, 27) because of the flux which remains constant.

It is understood that the foregoing description is that of the preferred embodiments of the invention and that various changes and modifications may be made thereto without departing from the spirit and scope of the invention as defined in the appended claims.

What is claimed is:

1. Apparatus for determining the proportion of a substance having paramagnetic properties in a mixture of substances, the apparatus comprising:

a housing having an interior and defining a longitudinal axis and said housing having a first longitudinal end and a second longitudinal end;

a cuvette rotatably mounted in said housing between said ends for rotation about said axis and defining a plane of rotation partitioning said interior of said housing into first and second component regions;

said cuvette having first and second rotating surfaces facing toward said first and second component regions, respectively;

said cuvette having a plurality of cells for receiving the mixture of substances containing the paramagnetic substance;

an even number multiple of magnetic field cores mounted in said first component region of said housing for conducting a magnetic field which penetrates said cells of said cuvette;

a drive unit mounted at said first longitudinal end and having a drive shaft connected to said cuvette for rotating said cuvette past said cores whereby said paramagnetic substance in said cells causes magnetic flux changes;

a plurality of measuring field coils surrounding said cores, respectively, for converting said magnetic flux changes into an electrical signal and said magnetic field cores being aligned in a direction toward said cuvette; and, magnetic field supply means for supplying said magnetic field and said magnetic field supply means being mounted in said second component region of said interior of said housing said magnetic field supply means being formed as a permanent magnet and having a first magnetic pole face of a first polarity connected directly to said housing whereby said housing assumes said first polarity;

said magnetic field supply means having a second magnetic pole face of a second polarity facing toward said second rotating surface of said cuvette and said second magnetic pole face defining a pole face surface which is essentially completely coextensive with said second rotating surface;

said magnetic field cores being positioned in said first component region so as to be directed toward said cuvette and having respective first end faces connected directly to said housing so as to cause said magnetic field cores to likewise assume said first polarity; and, said magnetic field cores having respective second end faces also having said first polarity and said second end faces being adjacent said first rotating surface of said cuvette and opposite said second magnetic pole face of said second polarity.

2. The apparatus of claim 1, wherein each of said magnetic field cores and said measuring field coils corresponding thereto have a magnetization polarity; and, wherein the magnetization polarity of said magnetic field cores and their respective measuring field coils is combined in alternate alignment with the magnetization polarity of the next adjacent magnetic field cores and their respective measuring field coils.

3. The apparatus of claim 1, further comprising a plate made of good magnetically conducting material and defining an equipotential surface; and, said plate being mounted on said second magnetic pole face of said magnetic field supply means.

4. The apparatus of claim 3, said plate being made of highly permeable iron-cobalt alloy.

5. The apparatus of claim 1, said cuvette comprising a circular disc having cutouts defining said cells and through which said mixture of substances flows; and, said cutouts being positioned in said circular disc so as to be symmetrical to said axis and said cutouts having respective contours configured such that for a position of one of the cutouts in which the second end face of one of the magnetic field cores is fully exposed, the second end face of the next adjacent magnetic field core remains excluded from the region within the contour of said one cutout; and, said contours being further configured such that the sum of the cross sections of the second end faces which are only partly exposed by the contours of said cutouts remains essentially constant in the course of the rotational movement of said circular disc.

6. The apparatus of claim 5, said cutouts being circular annular segmented cutouts concentric to said rotational axis.

7. The apparatus of claim 5, said cutouts having a kidney-shaped contour and extending concentrically to said rotational axis.

* * * * *

UNITED STATES PATENT AND TRADEMARK OFFICE
CERTIFICATE OF CORRECTION

PATENT NO. : 5,391,986
DATED : February 21, 1995
INVENTOR(S) : Thomas Sauerbaum

It is certified that error appears in the above-indentified patent and that said Letters Patent is hereby corrected as shown below:

On title page, item [56], "U.S. Patent Documents", delete "3,537,713" and substitute -- 3,539,913 -- therefor.

In column 1, line 52: delete "coil." and substitute -- coils. -- therefor.

In column 3, line 10: delete "high" and substitute -- highly -- therefor.

In column 4, line 39: delete "site" and substitute -- same -- therefor.

In column 5, line 50: after "housing", insert -- ; --.

Signed and Sealed this

Twenty-fifth Day of April, 1995

Attest:

BRUCE LEHMAN

*Attesting Officer*     *Commissioner of Patents and Trademarks*